United States Patent [19]

Filip

[11] Patent Number: 5,424,068

[45] Date of Patent: Jun. 13, 1995

[54] METHOD FOR IMMUNIZATION OF MAMMALS AGAINST ATHEROSCLEROSIS AND PHARMACEUTICAL COMPOSITIONS FOR OBTAINING SAID IMMUNIZATION

[75] Inventor: Doina Filip, Bucarest, Romania

[73] Assignee: P. Doina International Ltd., Haifa, Israel

[21] Appl. No.: 27,502

[22] Filed: Mar. 5, 1993

[30] Foreign Application Priority Data

Dec. 7, 1992 [IL]  Israel ..................................... 104015

[51] Int. Cl.$^6$ ..................... A61K 37/20; A61K 37/22
[52] U.S. Cl. ................................ 424/278.1; 424/283.1
[58] Field of Search ..................... 424/88, 520, 278.1, 424/283.1

[56] References Cited

U.S. PATENT DOCUMENTS 4,891,220  1/1990  Donzis ................................. 424/88

OTHER PUBLICATIONS

Joseph L. Witztum 1993. Role of oxidised low density lipoprotein in atherogenesis. British Heart journal No. 69 Supplement pp. S12–S18.
Fusion of Low Density Lipoproteins with Cholesteral Ester-Phospholipid Microemulsions, Parks et al. J. Biol Chem. 1985 260(5)3155–63.
Modification of Low Density Lipoproteins by Secretaoy Granules of Rat Serosal Mast Cells Kovanen and Kokkonen 1991 266(7):4430–36 J. Biol. Chem.
Technological Advances in Vaccine Development ed. Laurence Lasky ©1988 pp. 401–409.
"Biology of Disease—The Pathogenesis of Atherosclerosis: Atherogensis and Inflammation", by J. Michael Munro et al. Laboratory Investigation, vol. 58, No. 3, pp. 249–261, 1988.
"Cellular Events in the Development of Valvular Atherosclerotic Lesions Induced by Experimental Hypercholesterolemia", by Doina A. Filip et al, Atherosclerosis, vol. 67, pp. 199–214, 1987.
"Possible Role of Macrophages in Regression of Atherosclerosis", by Eugen Koren et al, Prog. Lipid Res., vol. 30, No. 2/3, pp. 237–243, 1991.
"Rates of Receptor-Dependent and -Independent Low Density Lipoprotein Uptake in the Hamster", by David K. Spady et al, Proc. Natl. Acad. Sci. USA, vol. 80, pp. 3499–3503, Jun. 1983.
"Preparative and Quantitative Isolation of Plasma Lipoproteins: Rapid, Single Discontinuous Density Gradient Ultracentrifugation in a Vertical Rotor", by Byung H. Chung et al, Journal of Lipid Research, vol. 21, pp. 284–291, 1980.
"Minimally Modified Low Density Lipoprotein Stimulates Monocyte Endothelial Interactions", by Judith A. Berliner et al, J. Clin. Invest., vol. 85, pp. 1260–1266, Apr. 1990.
"Long-Term Experience with Extracorporeal Low--Density Lipoprotein Cholesterol Removal by Dextran Sulfate Cellulose Adsorption", by P. Schulzeck et al, Clin. Investig., vol. 70, pp. 99–104, 1992.
"The Hyperlipidemic Hamster as a Model of Experimental Atherosclerosis", by Anca Nistor et al, Atherosclerosis, vol. 68, pp. 159–173, 1987.

*Primary Examiner*—Christine M. Nucker
*Assistant Examiner*—Nita M. Minnifield
*Attorney, Agent, or Firm*—Lowe, Price, LeBlanc & Becker

[57] ABSTRACT

Pharmaceutical compositions and a method for immunization of mammals against atherosclerosis including steps of a) obtaining blood from a mammal; b) isolating low density lipoprotein from the blood; c) fusing the lipoprotein in vitro to obtain heavy microemulsion lipoprotein fusion particles having new antigenic determinants; d) administering the fusion particles obtained in step (c) to a mammal; and e) allowing the immune system to clear fusion lipoprotein particles from the mammal.

14 Claims, 8 Drawing Sheets

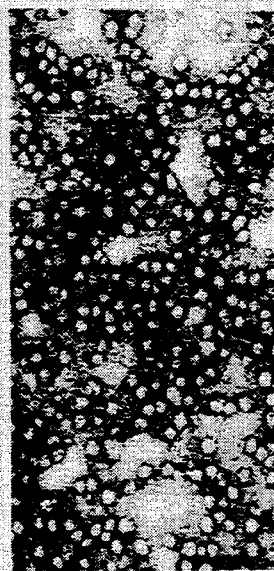
FIG.2A  FIG.2B
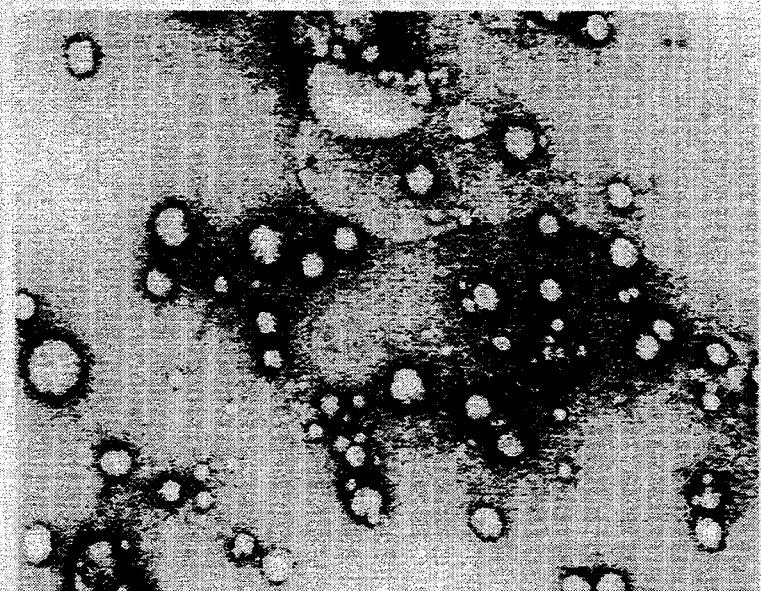
FIG.2C

FIG.5A
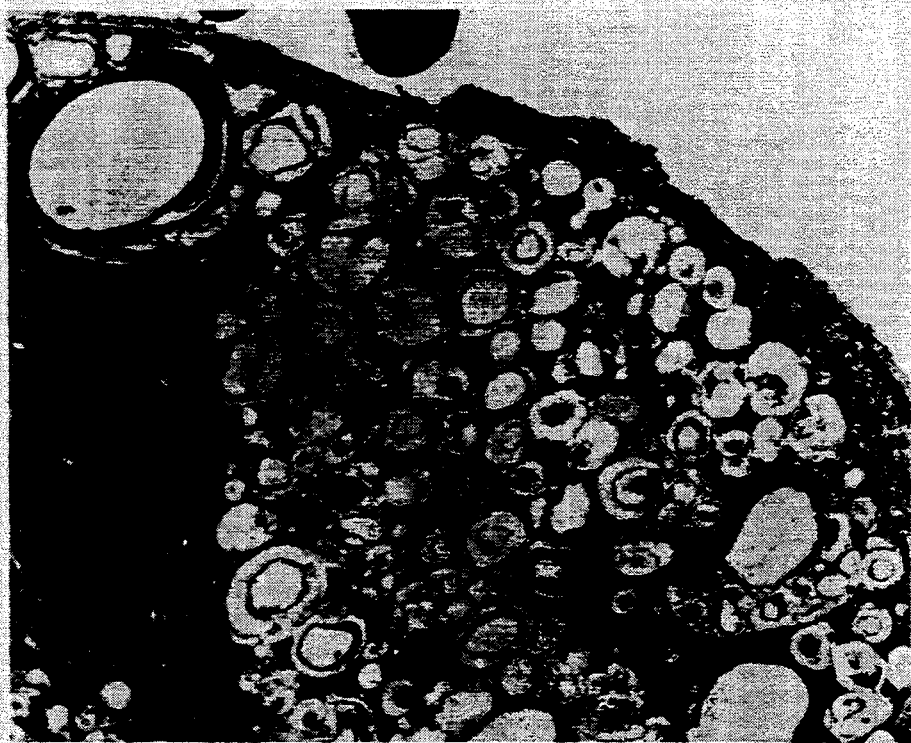
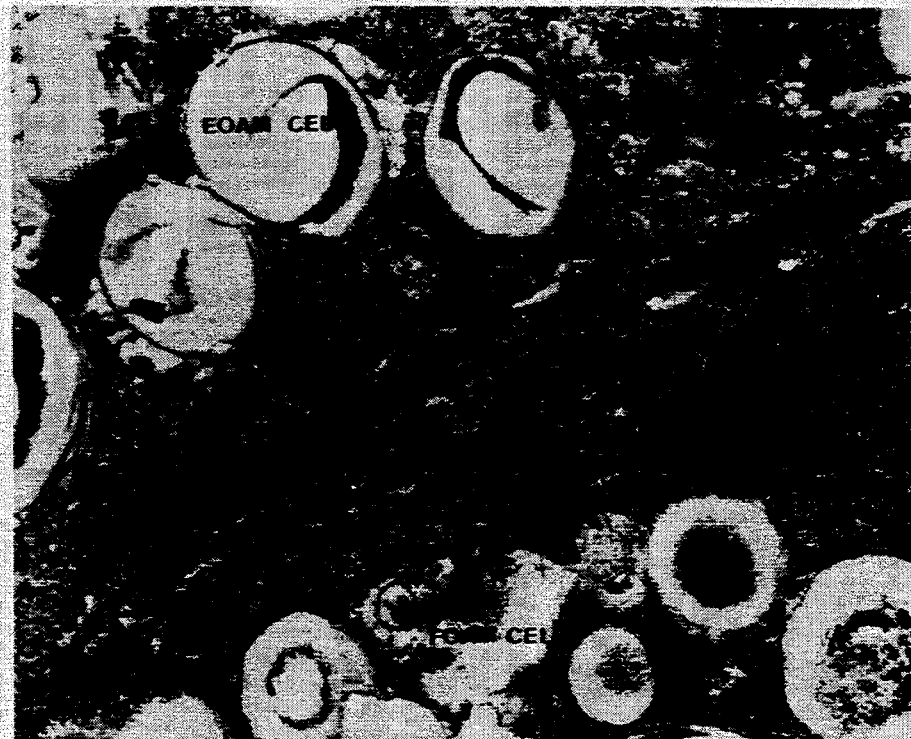
FIG.5B

METHOD FOR IMMUNIZATION OF MAMMALS AGAINST ATHEROSCLEROSIS AND PHARMACEUTICAL COMPOSITIONS FOR OBTAINING SAID IMMUNIZATION

FILED OF THE INVENTION

The present invention relates to a method for immunization of mammals, particularly humans against atherosclerosis. The present invention also relates to pharmaceutical compositions for the treatment and for prophylaxis of atherosclerosis and to a method for the preparation of said pharmaceutical compositions. Said invention also relates to a method for treatment of atherosclerosis in mammals.

SUMMARY OF THE INVENTION

The present invention relates to a method for immunization of mammals against atherosclerosis comprising the following steps; a) obtaining blood from said mammal; b) LDL isolation from said blood; c) LDL fusion in vitro providing heavy microemulsion particles; d) administering to said mammal the microemulsion obtained in vitro.

Said invention relates also to pharmaceutical compositions for treatment of atherosclerosis and for prophylaxis of atherosclerosis comprising as an active ingredient a reorganized lipid material originating from the mammal to be treated and a conventional immunization adjuvant product.

The present invention also relates to a method for the preparation of said pharmaceutical compositions wherein the reorganized lipid material is obtained by adding an amphipathic material to the patient lipoprotein in vitro to fuse the lipoprotein and then removing said material out.

Said invention also relates to a method for treatment of atherosclerosis in mammals according to conventional immunization scheme comprising administering the above-mentioned pharmaceutical compositions to the patient's body and subsequently the same conventional immunization procedure is applied to the patient's body at two week or other convenient intervals.

BRIEF DESCRIPTION OF THE FIGURES

FIGS. 2a-2e show the characteristics of the LDL fusion particles of the present invention.

FIG. 3b shows numerous plasma cells (x 29,400), which surround the extracellular accumulations of lipid materials. These cells have the characteristic distended rough endoplasmic reticulum, indicative of antibody synthesis FIG. 3C (inset)(X 59,600).

FIG. 5a shows that at 30 days of diet, the foam cells are massively egressing from the tissue (X 8,300).

FIG. 5b shows that foam cells have specialized interdigitized structure, egressing a cooperative action in the region of the endofilial cell Junctions (X 29,400).

BACKGROUND OF THE INVENTION

Figure 1:
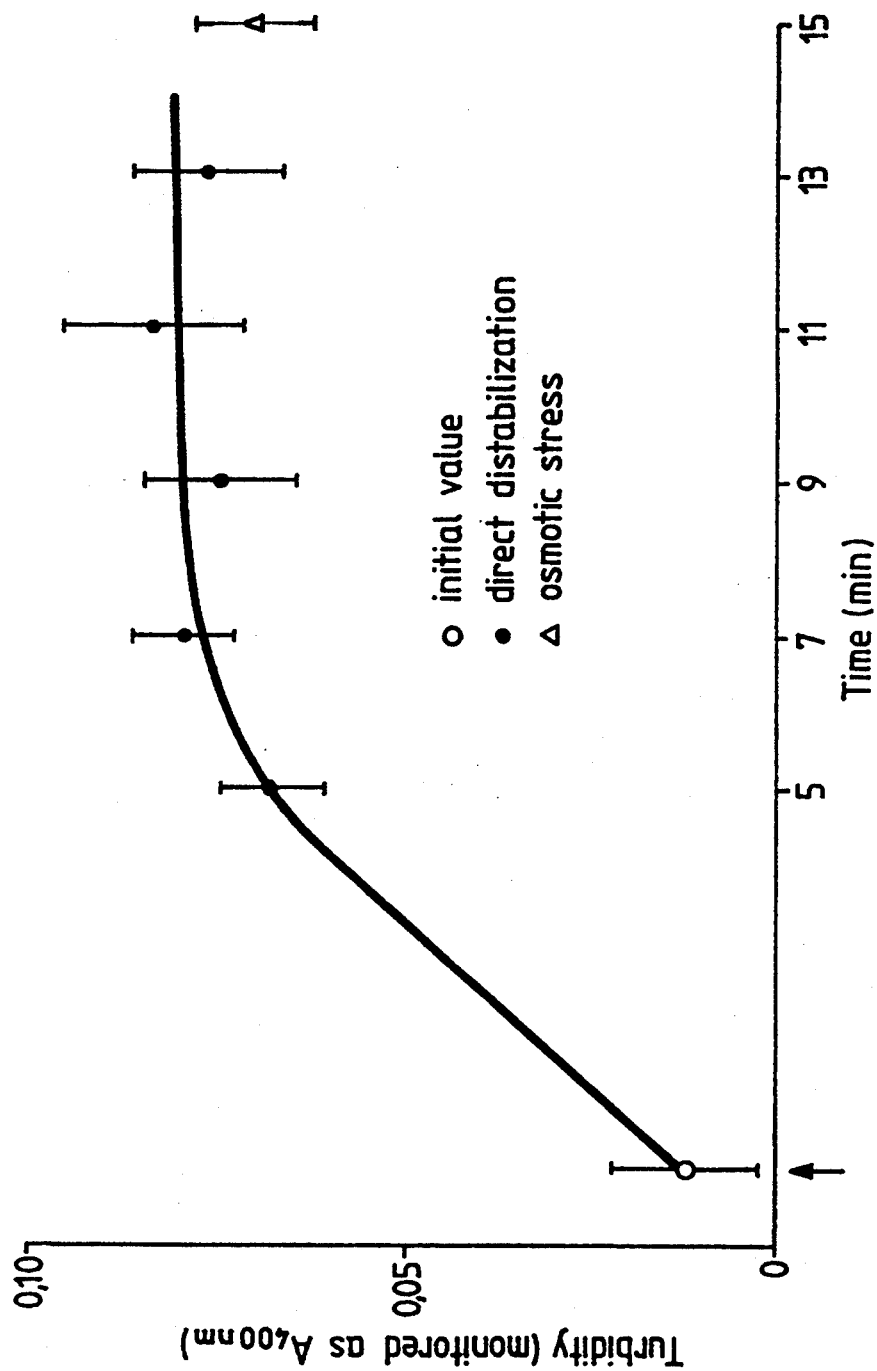
FIG. 1 shows the process of hamster LDL fusion by vacitrasin, monitored as absorption at 400 nm (black circles).

Atherosclerosis is a degenerative disease affecting the entire human population. It is brought about by a change in the normal structure of the blood vessels, especially in the areas known as lesion-prone, located at vessel branching points, or in the regions where the blood flow is turbulent due to the morphology of the human circulatory system. This change is represented by an accumulation of extracellular lipids, accumulation of lipid-laden macrophages (foam cells), proliferation of vascular smooth muscle cells and an accumulation of extracellular matrix. All these changes reduce the vascular lumen and may finally obstruct the vascular flow, with all known pathological consequences.

A population especially at risk are the familial hypercholesterolemics, who have a defective apolipoprotein B receptor. In this genetic disease, there is an increased quantity of circulating low density lipoproteins (LDL), the main cholesterol carrier in the human body. Its clearance from the circulation is impaired due to the defective receptor. Consequently, there is also an increased transport of the LDL into the vessel intima, by non-receptor mediated transport. The excess of LDL in the vessel intima of these patients gives rise to increased frequency of atherogenic lesion formation and an increase in the dimensions of these lesions.

The treatments now in use for this disease are intended (i) to lower the circulating cholesterol level (and, implicitly the LDL circulating level), and this is the case of lipid-poor diets and of the lipid-lowering drugs and (ii) to counteract the modifications which are considered to make the LDL more atherogenic, which is the case of the antioxidants of probucol and carotene type. The more extreme case of the genetic hyperlipidemias may require a treatment by the two above procedures, but combined with the reducing of circulating cholesterol level by LDL apheresis (Scholzek, P. et al. Clinical Investigator, 1992, 70, 99).

The present proposed method for atherosclerosis treatment is based on an entirely different principle, implying an immunization against the first form of lipid reorganized material appearing in the lesion-prone areas. As a consequence the immune system reacts very rapidly against the lipid material in the lesions which is taken out by a monocyte clearance system based on an immune mechanism. Moreover, the existence of an immune-based mechanism for lipid clearance determines a reversion of the lesion-prone areas to their normal state, irrespective of the circulating cholesterol level. This is achieved in a time which is approximately equivalent to the 1/100th of the lesion development time and the balanced situation of the vessel is maintained from this point on.

DETAILED DESCRIPTION OF THE INVENTION

The reorganized lipid material in the atherogenic lesions according to the present invention is formed by a LDL fusion process in the vascular intima. The fusion process of the LDL produces heavy microemulsion droplets with increased dimensions and multiple apolipoprotein B copies on their surface, a situation in which new antigenic determinants of the apolipoprotein B are exposed, rendering the heavy microemulsion particle antigenic and immunogenic. The term "heavy microemulsion particle" as used throughout the specification means a microemulsion particle having a flotation density of about 1.00-1.24 g/ml.

The fusion of the LDL was obtained in vitro in simple conditions not implying the modification of the LDL native state with regard to its oxidation state and reproducing simple ionic conditions most probably existing in an intima undergoing an atherogenic transformation. By immunizing experimental normal animals such as hamsters with this material containing only the reorganized lipid material of the LDL in a physiological saline, emulsified in a conventional adjuvant product it was possible to select specific B and T lymphocyte clones capable of reacting against a similar type of reorganized LDL material, immediately after its formation in the lesion-prone areas of the animals on an atherogenic diet. The Syrian golden hamster was used (Nistor, A., et al., Atherosclerosis, 1987, 68, 159), because of the great similarities between its lipoprotein metabolism and the human lipid metabolism (Spady, D. K., et al., Proc. Natl. Acad. Sci., USA, 1983, 80, 3499). Moreover, this animal was shown to develop obstructive coronary lesions at long diet times.

The important advantage of this procedure is that the reorganized form of LDL exists only in the lesional areas, and these areas are the only target of the immune-competent lymphocyte clones selected by the immunization. By the immunization a reversion of the affected lesion-prone areas to the normal structure is induced and maintained. This management of the atherogenic lesions can be applied both prophylactically and therapeutically, as will be detailed below. The normal LDL metabolism is not affected, since the circulating form of the lipoprotein is the unmodified form.

The LDL fusion in vivo is a lipoprotein modification leading to an increased capacity of the native LDL-based material to generate atherogenic lesions. The essence of the present invention is the development of a LDL fusion procedure in vitro, leading to a LDL-based material which is identical to the in vivo material. This type of material is both antigenic and immunogenic (i.e., it represents a non-self structure which has the capacity to select specific lymphocyte clones producing antibodies against it). Such a statement is based on the reaction of the immune system against the extracellular lipid material in the lesions, when the immunization and the diet were applied sequentially.

The detailed procedure for the LDL fusion is the following:

1. LDL isolation and characterization (standard methods were applied for said LDL isolation and characterization).

From the experimental animals the blood was obtained by cardiac puncture. From human subjects (blood donors) the blood was obtained by phlebotomy in standard conditions, after their informed consent. Plasma was immediately obtained by low speed centrifugation. The LDL fraction was obtained from fresh plasma by single vertical spin density gradient ultracentrifugation (Chung, B. H., et al., J. Lipid Res., 1980, 21, 284). The LDL purity was checked by immunochemical methods using affinity-purified anti holoLDL polyclonal antibodies. The native state of the LDL was checked by the high performance liquid chromatography (HPLC) quantitation of its molondialdehude (MDA) content. The level found characterized the isolated lipoprotein as native (Berliner, J. A., J. Clin. Invest., 1980, 85, 1260). The integrity of the LDL apolipoprotein B, characterizing its native state was also checked by sodium dodecyl sulfate polyacrylamide gel electrophoresis (SDS-PAGE).

2. LDL fusion in vitro

The LDL was transferred into half-diluted phosphate-buffered saline (PBS) containing 72 mM Na+, 2 mM K+, 0.3 nM Mg2+, 0.45 mM Ca2+, by gel filtration on a 2 ml Sephadex G-25 column. The concentration of Ca2+ was raised to 1.6 mM. These ionic concentrations are characteristic for the physiological saline solution used as a fusion buffer (FB). This buffer was found to be essential for the fusion procedure.

It was found that LDL fusion may be obtained by two methods based on entirely different physico-chemical phenomena.

The first method used the antibiotic bacitracin to fuse the lipoprotein. One of the unique properties of bacitracin is its pronounced amphipathic activity. Said antibiotic material was then taken out from the fused preparation by a simple dialysis, due to its small molecular weight. After the dialysis the total removal of the antibiotic from the preparation was demonstrated by a specific bacitracin quantitation HPLC method. (See Pavli, V.; Sokolic, M., J. Lig. Chromatogr., Vol. 134 (1990), pp. 303-310). The same fusion effect was also induced by the neurohormone vasopressin, having similar structural features with the antibiotic bacitracin, at steady-state concentration levels found usually in the human plasma.

The second method of LDL fusion was based on osmotic stress inducing the fusion process by osmoelastic coupling. The osmotic stress was generated by subjecting the LDL, transferred in FB to a dialysis against 20% polymer solutions of polyethylene glycol (PEG) 20,000 or dextran 40,000.

EXPERIMENTAL DATA

The in vitro work below was done for animal and human material. Only the immunization work was done solely in animals.

DETAILED DESCRIPTION OF THE FUSION METHODS a. Fusion by bacitracin. To 0.1-0.7 mg/ml LDL in FB, bacitracin was added from a fresh 70 mM solution to a final concentration of 0.35 mM and the preparation was incubated at 20° C. for 15 min. The best fusion yield was obtained at a bacitracin to apolipoprotein B ratio of 7.5. At the end of the incubation period the Ca2+ was chelated with ethylene diamine tetraacetic acid (EDTA) (2 mM final concentration). An extensive dialysis of the preparation against 4,000 volumes of PBS followed. This dialyzed preparation was used for the immunization.

b. Fusion by vasopressin. To 0.1–0.7 mg/ml LDL in FB, vasopressin (Sigma Chemical Co., USA) was added from a fresh 1 mg/ml solution at the final concentration of 2 pg/ml and the preparation was incubated at 20° C. for 30 min. An extensive dialysis against 4,000 volumes of PBS followed.

c. Fusion by osmotic stress. The 0.1–0.7 mg/ml LDL solution in FB was subjected to a 15 min. dialysis at 20° C. against a 20% solution of PEG 20,000 or dextran 40,000 in water. The cutoff limit of the dialysis bag was 10,000. An extensive dialysis against 4,000 volumes of PBS followed.

Bacitracin produced the LDL fusion in the presence of 1.6 mM Ca2+ in 7 min.; the equilibrium was attained for hamster LDL in 15 min. and for human LDL in 20 min. This was indicated by the turbidiby of the sample, monitored spectrophotometrically by absorption at 400 nm (FIG. 1). Bacitracin was effective in inducing the LDL fusion from 0.35 mM to 0.35 pM. The concentration of vasopressin tested was in the physiological range (2 pg/ml).

Figure 2D:
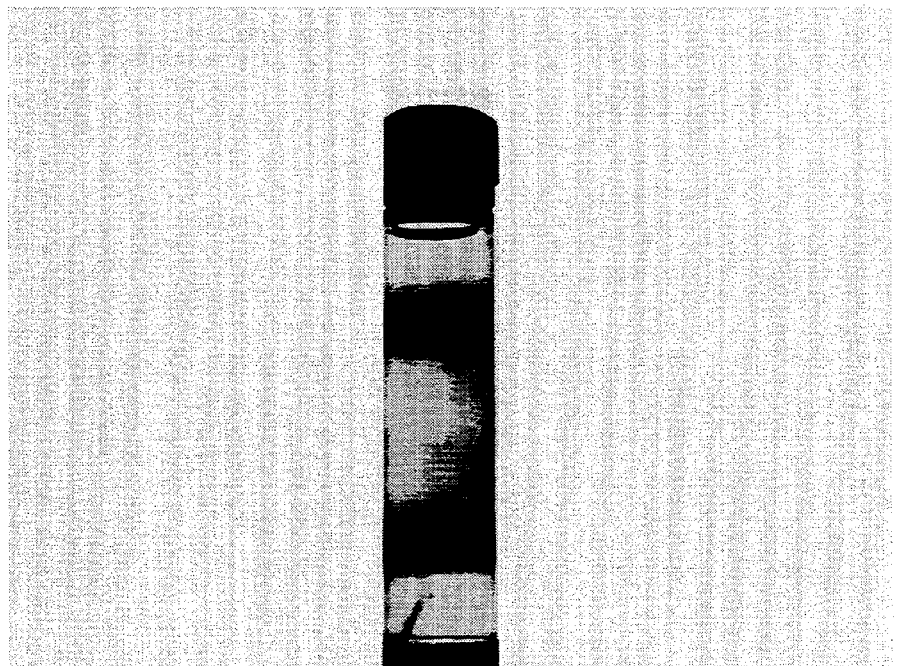

The fusion phenomena were observed ultrastructurally by negative staining. The LDL preparation was formed from 20 nm particles of uniform size (FIG. 2A), floating at 1.06 g/ml in the gradient density ultracentrifugation (FIG. 2B). The fused preparation was formed from microemulsion droplets with dimensions ranging from 30 to 300 nm (FIG. 2C), floating in two bands at 1.21 and 1.24 g/ml (FIG. 2D). The dimensions and the flotation densities of the microemulsion droplets in the fused preparations were similar to the material isolated from the experimental hamster atherogenic lesions. It was also concluded that the change in the flotation density in both in vivo and in vitro material was due to the presence of multiple copies of apolipoprotein B on the surface of the microemulsion droplets. This conclusion was based on a correlative investigation of both in vivo and in vitro material from the experimental animals and of in vitro studies for the human material; this correlative investigation comprised biochemistry, cytochemistry, immunochemistry, electron microscopy and work in vitro with isolated cells (hamster monocytes).

Figure 2E:
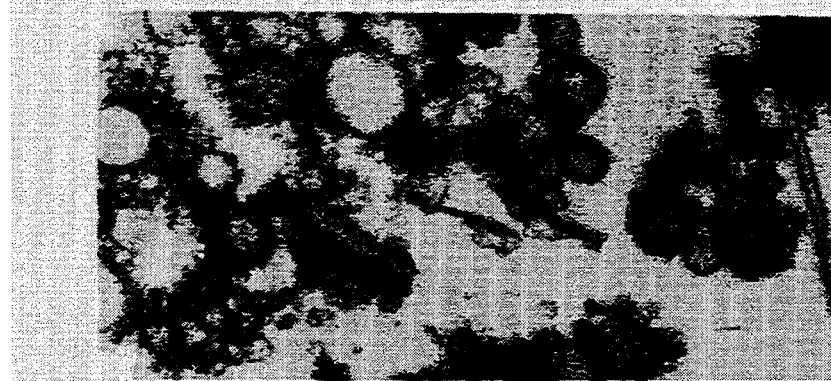

The heavy microemulsion particles proved to have the same pattern of organization as the LDL: a core of neutral lipid stabilized in a hydrophilic medium by a phospholipid monolayer (FIG. 2E) in which multiple copies of the apolipoprotein B were embedded. By taking the LDL parameters as a basis, an estimation of the droplet surface/LDL surface would predict 2 copies of apolipoprotein B on the surface of a 30 nm particle and 225 copies on the surface of a 300 nm particle. This novel rearrangement of self molecules proved to be antigenic and immunogenic.

Animals were immunized by a conventional immunization scheme comprising a primary immunization with 50 μg of protein/animal (mean weight 100 g) and three secondary immunizations at two-week intervals with 25 μg of protein each, with the microemulsion obtained in vitro; a group was hyperimmunized and received 7 secondary immunizations. Then, these animals were given a hypercholesterolemic diet in the form of standard hamster chow supplemented with 5% cholesterol and 15% butter, for 7, 14, 30 and 60 days. After these diet times, 2–3 ml of blood were obtained by cardiac puncture for biochemical and immunochemical investigation, then the animals were sacrificed for the ultrastructural investigation of their lesions.

The total cholesterol determinations in the sera of these animals indicated clearly their hypercholesterolemic state, by comparison with the values obtained from the atherogenic control animals. The only significant deviation from the control values was at 7 and 14 days of diet, when a significant increase in the level of circulating cholesterol was observed. The explanation of this increase in the level of circulating cholesterol was due to an immunosuppression phenomenon because of the unfused LDL present in the preparation. This immunosuppression was not present in the case of animals immunized with fused human LDL (Table 1).

TABLE 1

| | Cholesterol values in the experimental atherogenic animals (mg/dl) | | | | |
|---|---|---|---|---|---|
| Normal | (pooled sera) Control | Atherogenic | Immunized | Hyperimmunized | Immunized with human fused LDL |
| 103 ± 7 | 150 | (7 days diet) | 327 ± 72 | — | 126 ± 38 |
| | 200 | (14 days diet) | 419 ± 73 | — | 146 ± 16 |
| | 250 | (30 days diet) | 258 ± 49 | 240 ± 76 | 244 ± 13 |
| | 300 | (60 days diet) | 352 ± 96 | — | |

After this initial increase the cholesterol level dropped and reached the values comparable to that of the atherogenic unimmunized control.

The circulating antimicroemulsion antibody titers determined by conventional enzyme-linked immunosorbent assay (ELISA) showed measurable, but very low, antibody titers (2 to −3) only at 7 days of diet. At all the other diet times, no measurable levels of circulating antibodies were detected, indicating that the immune reaction was localized to the lesional areas, as it will be detailed below. The cross-reactivity of the sera from the antigen-challenged animals (immunized animals receiving an atherogenic diet) with the homologous LDL was tested and a negative result was obtained.

Figure 3A:
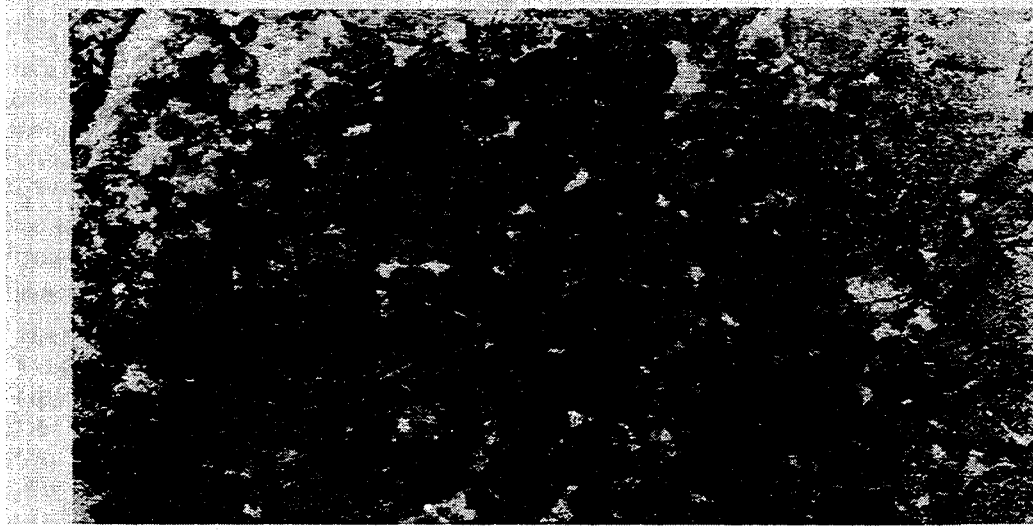
FIG. 3a shows that in immunized animals, starting with the first week of hypocholesterolemic diet post-immunization, the lipid material in the microemulsion form is stable as in comparison with the control hypocholesterolemic animals, in which the same type of material is in a dynamic state of liquid component reorganization (x 95,400).

The effect of the immunization was tested on lesion development in the region of the aortic valve rings. This area was particularly susceptible to the atherogenic diet, developing fibrolipidic-like lesions 10 times faster than any other lesion-prone areas in the hamster. The main body of these lesions was formed by the extracellular lipid material in a very dynamic state of lipid component rearrangement. In the antigen-challenged animals at 7 days of diet, the lesions developed in the above locations, implying that the LDL metabolism in these animals was not affected, being similar to the control atherogenic animals. At this time of diet, in the controls, the extracellular lipid material was in the form of densely packed microemulsion droplets in a dynamic state of reorganization. In the antigen-challenged animals the microemulsion lipid material was stabilized (FIG. 3A) and numerous plasma cells surrounded the lipid deposits (FIG. 3B). They had characteristic distensions of their endoplasmic reticulum, indicating an active antibody synthesis (FIG. 3B, inset). The reaction of the immune system to the microemulsion droplet material in the lesions in the antigen-challenged animals implied an identity between the microemulsion droplet material formed in vivo in the lesions and the in vitro material used for the immunizations, since the diet was administered post-immunization. At 14 days of diet, the former fibrolipidic-like lesions developed in the unimmunized controls were replaced by a fatty streak (FIG. 4), implying that a reversion of the lesion type took place. This was not previously induced in any experimental model of atherogenesis by any type of experimental manipulation and is a process only presumed to take place naturally in humans in which, occasionally, lesional areas requilibrate (Munro, J. M. Cotran, R. S. Lab. Invet., 1988, 58, 249). At 30 and 60 days of diet, 80% of the aortic ring area had an aspect close to the normal. Moreover, the clearance of the area was assured by numerous monocyte-derived from cells, showing morphological specializations which clearly indicated a close cooperation in their egression from the tissue (FIGS. 5A and 5B).

In the animals immunized with the fused human LDL the same trend of events was observed, and the presence of antibody secreting B cells was the same around the lesions. Consequently the same reversion events took place and at about 1 month of diet the vessel returned to its normal structure.

Figure 6A:
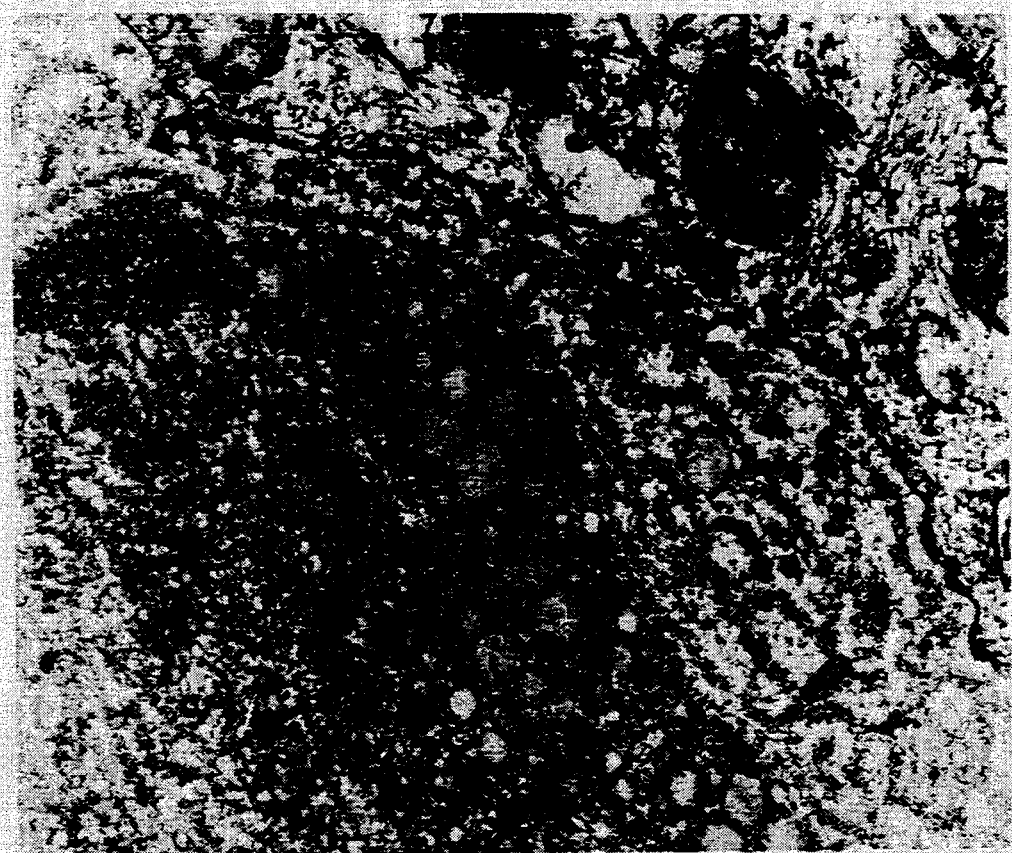
FIG. 6a shows that at 30 days of diet post-immunization, the lesional area is already re-equilibrated between the microemulsion droplet material formation and its disposal by the foam cell egression, resulting in a normal aspect of the lesion-prone area (X 54,600).
Figure 6B:
FIG. 6b shows the aspect of the same area in the normal control animals, in which some microemulsion droplets can be seen immediately under the endothelial cells; their presence reflects the very high propensity of this area to develop atherogenic lesions (X 37,800).
Figure 6C:
FIG. 6c shows the same region in the control immunized animals not receiving an atherogenic diet (X 54,600).

In the hyperimmunized animals, at 30 days of antigen-challenge post-immunization, the structure of the aortic ring area was normal, as compared to the normal animals (not immunized and receiving a normal diet) and with the immunized controls (immunized animals receiving a normal diet) (FIGS. 6A, 6B, 6C).

Figure 7A:
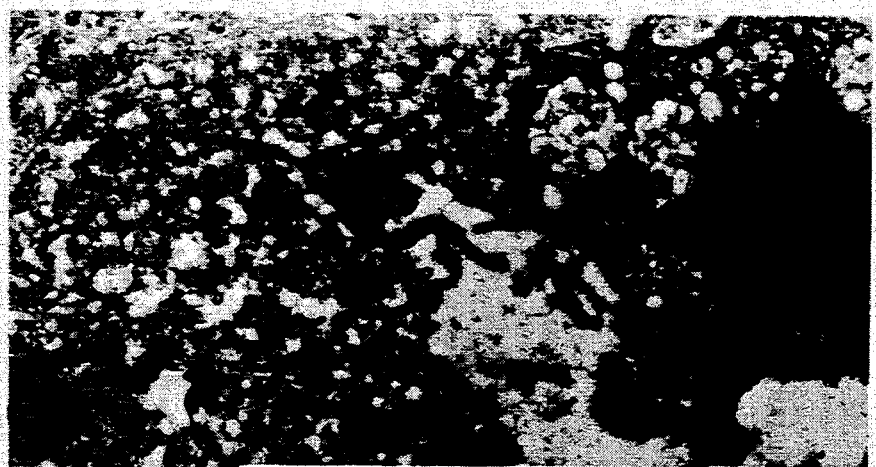
FIG. 7a shows the aspect of the lesions in the animals receiving the immunization post-diet.

In a special group of animals, the immunization was applied post-diet to elucidate if the same reversion process could be induced. After 3 months of atherogenic diet these animals had a total plasma cholesterol of 281+95 mg/dl. By taking into consideration the moment of activation of the resident valvular macrophages into presenting the antigen, a process which appears from the first week of diet in the antigen-challenged animals and appears very late (6 months) in the course of atherogenic lesion development (Filip, D. A., et al. Atherosclerosis, 1987, 67, 199) a working hypothesis indicated that a reasonable moment to check the eventual reversion was at 1/10 of the total diet time from the moment the immunization was completed (the immune surveillance system established). A considerable degree of reversal was obtained in comparison with the atherogenic controls (FIG. 7A). However, the previous diet period left sequellae, representing the effects of lipid component reorganization (FIG. 7B). Nevertheless, even the reorganized lipid material in the form of micronic cholesteryl ester droplets (FIG. 7B) was taken up by the monocyte/macrophages in the same time with the phagocytosis of the heavy microemilsion formed in vivo by the fusion. The mechanism of disposal of cholesteryl ester micronic droplets was similar to the one observed in vitro during the incubation of monocyte/macrophages with cholsterol crystals (Koren, E. et al., Prgo. Lipid Res., 1991, 30, 237). It consisted in the surrounding of the cholesteryl ester micronic droplets with multiple phospholipid bylayers (FIG. 7B, inst) micronic.

In conclusion, it appears that the immunization against a heavy microemulsion formed by the LDL fusion and representing the initial step in the extracellular lipid accumulation in the atherogenic lesion-prone areas, reversed the atherogenic evolution by blocking its initial step. This immunological approach proved beneficial for the management of atherogenic lesions even if applied in advance or post-diet. Therefore, this approach may represent even a prophylactic or a therapeutic method of atherogenesis treatment by an immunological mechanism which is a vaccination.

DETAILED DESCRIPTION OF THE FIGURES

FIG. 1. The process of hamster LDL fusion by bacitracin, monitored as absorption at 400 nm (black circles). Each value represents the mean of triplicate aliqotes. As shown by the kinetics, the fusion is complete in 7 minutes and the equilibrium is attained in 9 minutes. For the human LDL the kinetics is somewhat slower, the fusion being complete in 15 min. and the equilibrium attained in 20 min. The same type of measurements were done for the initial and final absorption values in Stress-induced fusion experiments (triangle), also for hamster LDL.

FIG. 2. A. The LDL particles aspect in negative staining: the particles have similar dimensions around 20 nm (x 95,400). B. The LDL, separated by a single vertical spin density gradient centrifugation has a flotation density around 1.06 g/ml. C. The negative aspect of the LDL fused preparation, in which microemulsion droplets have dimensions between 30 and 100 nm (X 181,400). D. The microemulsion droplets, due to their high protein content (multiple apolipoprotein B copies on their surface) float at much higher densities (1.20 and 1.24 g/ml). E. The microemulsion droplets have the same pattern of organization as the lipoprotein, being composed of a core of neutral lipids, (evidenced here by a cytochemical reaction with tannic acid-paraphenuylene diamine) stabilized by a phospholipid monolayer (X 95,400).

FIG. 3. A. In the immunized animals, starting with the first week of hypercholesterolemic diet post-immunization, the lipid material in the microemulsion form is stabilized in comparison with the control hypercholesterolemic animals, in which the same type of material is in a dynamic state of lipid component reorganization (X 95,400). B. Numerous plasma cells (X 29,400), by ultrastructural criteria, surround the extracellular accumulations of lipid material; these cells have the characteristic distended rough endoplasmic reticulum, indicative of antibody synthesis C. (inset) (X 59,600).

Figure 4:
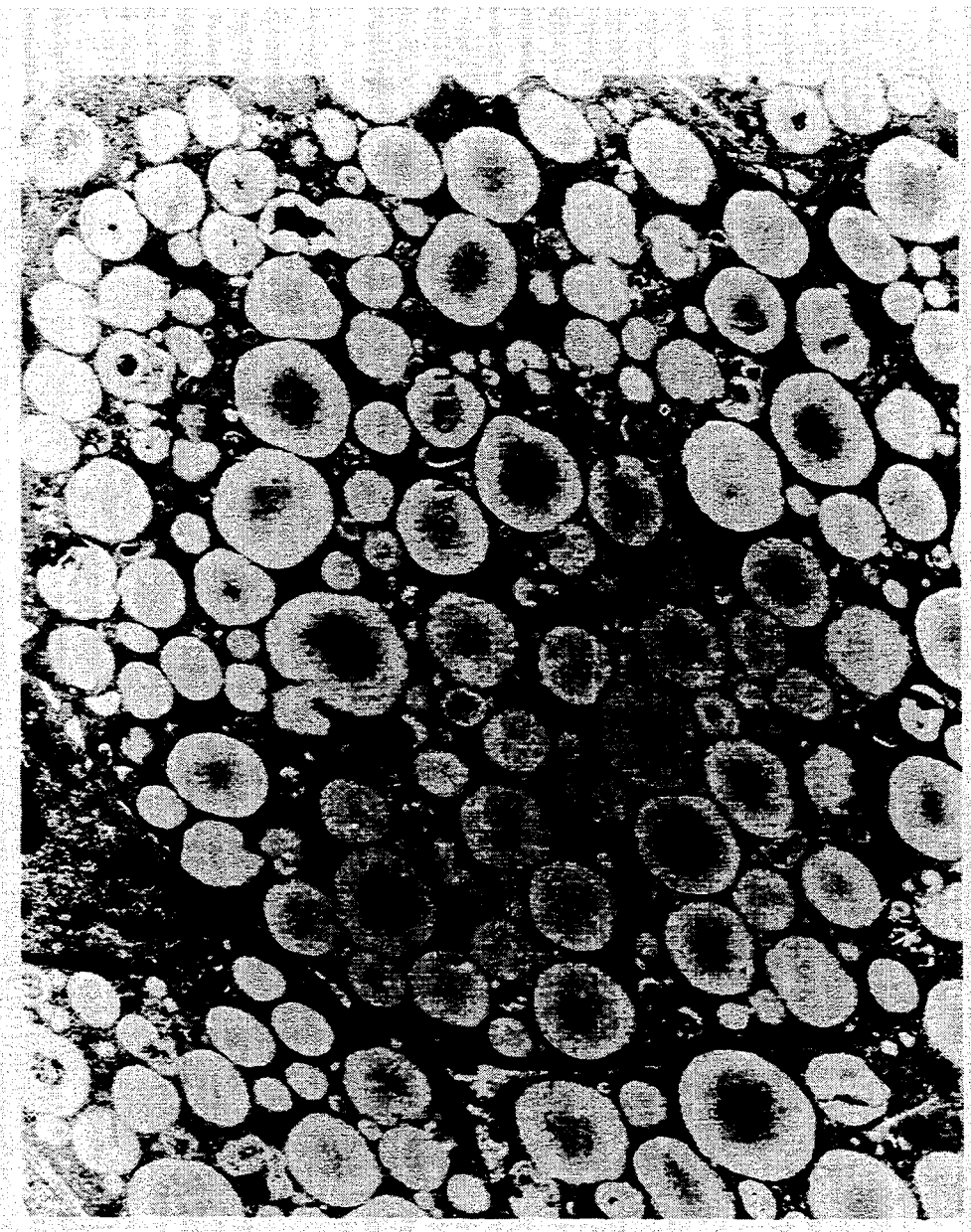
FIG. 4 shows at 14 days of diet, the previous fibrolipidic like lesions are transformed into fatty streaks.

FIG. 4. At 14 days of diet, the previous fibrolipidic-like lesions are transformed into fatty streaks. No more extracellular lipid material in microemulsion form is found extracellularly. This demonstrates the reversion of the previous fibrolipidic-like lesion to a more benign form of atherogenic lesions, namely the fatty streak.

FIG. 5. A. At 30 days of diet, the foam cells are massively egressing from the tissue (X 8,300). B. They have specialized interdigitized structure, assuring a cooperative action in the region of the endothelial cell junctions (X 29,400).

FIG. 6. A. In the case of hyperimmunized animals, at 30 days of diet post-immunization, the lesional area is already re-equilibrated between the microemulsion droplet material formation and its disposal by the foam cell egression, resulting in a normal aspect of the lesion-prone area (X 54,600). B. The aspect of the same area in the normal control animals, in which some microemulsion droplets can be seen immediately under the endothelial cells; their presence reflects the very high propensity of this area to develop atherogenic lesions (X 37,800). C. The same region in the control immunized animals, not receiving an atherogenic diet (x 54,600).

Figure 7C:
FIG. 7c shows the aspect of the lesions in the atherogenic controls, at approximately the same diet time period.
Figure 7B:
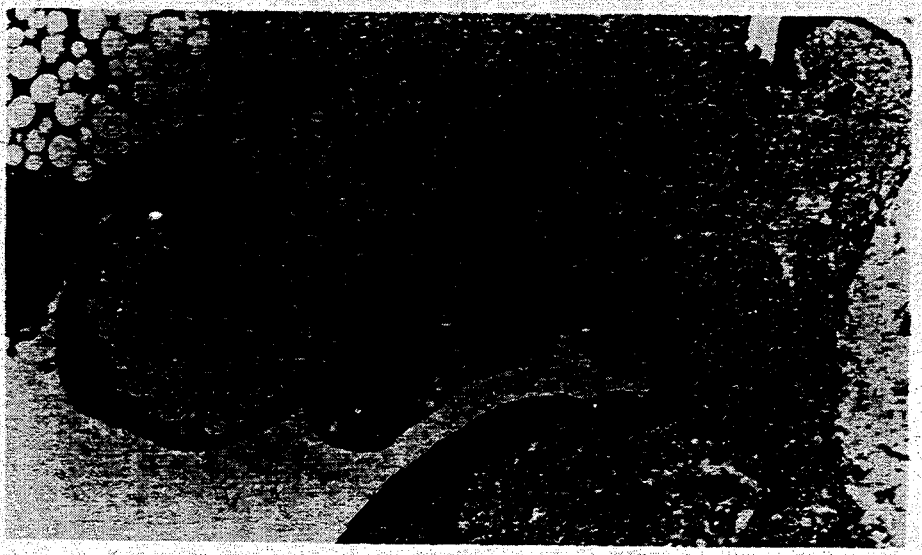
FIG. 7b shows a magnification of FIG. 7a at X 18,600.

FIG. 7. A. The aspect of the lesions in the animals receiving the immunization post-diet. The immunization was started after 3 months of atherogenic diet, and the animals were sacrificed at a total diet time of 17 weeks (at an 1/10 total diet time after the immunization scheme was completed). The lesion regression is evident, though the sequelae of the initial period of diet are present, especially in the form of cholesteryl ester droplets (X 54,600). However, even this type of material was disposed off by the monocyte/macrophages in the region, by a characteristic type of phagocytosis (B. inset) (X 18,600). C. The aspect of the lesions in the atherogenic controls, at an approximately the same diet time (X 3,600). All references cited herein are incorporated by reference.

I claim:

1. A method for immunization of mammals against atherosclerosis comprising the steps of:
   a) obtaining blood from said mammal;
   b) isolating low density lipoprotein from said blood;
   c) fusing said lipoprotein in vitro to obtain heavy microemulsion lipoprotein fusion particles having a flotation density of 1.20–1.24 g/ml and having new antigenic determinants;
   d) administering said fusion particles obtained in step (c) to a mammal;
   e) allowing the removal of heavy microemulsion particles from atherosclerotic lesions by immune mechanisms from said mammal.

2. A method for immunizing mammals against atherosclerosis according to claim 1, wherein said mammal is a human.

3. A method for immunizing mammals against atherosclerosis according to claim 1, wherein the step of fusing said lipoprotein comprises adding a surface active peptide with amphipathic properties to the lipoprotein and then removing said surface active peptide with amphipathic properties.

4. A method for immunizing mammals against atherosclerosis according to claim 3, wherein said surface active peptide with amphipathic properties is bacitracin or vasopressin.

5. A method for immunizing mammals against atherosclerosis according to claim 3, wherein said surface active peptide with amphipathic properties is removed by dialysis.

6. A method for immunizing mammals against atherosclerosis according to claim 1, wherein the step of fusing said lipoprotein comprises inducing the fusion process by osmotic stress to achieve osmoelastic coupling.

7. A method for immunizing mammals against atherosclerosis according to claim 1, wherein the step of fusing said lipoprotein further comprises carrying out fusion in the presence of a fusion buffer.

8. A method for immunizing mammals against atherosclerosis according to claim 1, wherein said heavy microemulsion particles have dimensions between 30 and 300 nm.

9. A pharmaceutical composition for the treatment of atherosclerosis and for prophylaxis of atherosclerosis comprising as an active ingredient a reorganized lipid material comprising heavy microemulsion particles having a flotation density of 1.20–1.24 g/ml and having new antigenic determinants which originated from the animal to be treated, and a conventional immunization adjuvant product.

10. A method for the preparation of a pharmaceutical composition for the treatment of atherosclerosis and for the prophylaxis of atherosclerosis comprising as an active ingredient a reorganized lipid material comprising heavy microemulsion particles having a flotation density of 1.20–1.24 g/ml and having new antigenic determinants which originated from the animal to be treated, and a conventional immunization adjuvant product comprising the steps:
   a) obtaining a fusion lipoprotein by adding an amphipathic material to a patient's lipoprotein in a fusion buffer in vitro to fuse said lipoprotein; and
   b) removing said amphipathic material to isolate said lipoprotein fusion product comprising heavy microemulsion particles having a flotation density of 1.20–1.24 g/ml at having new antigenic determinants and transfer it to a physiological saline by dialysis.

11. A method for the preparation of a pharmaceutical composition according to claim 10 wherein said reorganized lipid material is obtained by inducing a fusion process by osmotic stress to achieve osmoelastic coupling.

12. A method for the treatment of atherosclerosis in mammals by an immunization scheme comprising administering the pharmaceutical composition of claim 9 to a patient's body at two week intervals.

13. A method according to claim 12, wherein said composition is administered by injection.

14. A pharmaceutical composition according to claim 9, wherein said pharmaceutical composition is a vaccine.

* * * * *

UNITED STATES PATENT AND TRADEMARK OFFICE
CERTIFICATE OF CORRECTION

PATENT NO. : 5,424,068
DATED : June 13, 1995
INVENTOR(S) : FILIP

It is certified that error appears in the above-indentified patent and that said Letters Patent is hereby corrected as shown below:

Column 10, line 21, change "animal" to --mammal--;

Column 10, line 29, change "animal" to --mammal--.

Signed and Sealed this

Fifth Day of March, 1996

Attest:

BRUCE LEHMAN

Attesting Officer     Commissioner of Patents and Trademarks